(12) United States Patent
Gabbay

(10) Patent No.: US 6,582,464 B2
(45) Date of Patent: Jun. 24, 2003

(54) BIOMECHANICAL HEART VALVE PROSTHESIS AND METHOD FOR MAKING SAME

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/817,621

(22) Filed: Mar. 26, 2001

(65) Prior Publication Data

US 2001/0049555 A1 Dec. 6, 2001

Related U.S. Application Data

(63) Continuation-in-part of application No. 09/563,565, filed on May 3, 2000.

(51) Int. Cl.[7] .................................................. A61F 2/24
(52) U.S. Cl. ...................................... 623/2.38; 623/2.41
(58) Field of Search ............................... 623/2.38–2.42, 623/2.2–2.35, 2.11

(56) References Cited

U.S. PATENT DOCUMENTS

| | | | |
|---|---|---|---|
| 3,739,402 A | * | 6/1973 | Cooley et al. ............. 623/2.13 |
| 4,084,268 A | | 4/1978 | Ionescu et al. .................. 3/1.5 |
| 4,197,593 A | * | 4/1980 | Kaster et al. ............. 623/2.39 |
| 4,477,930 A | | 10/1984 | Totten et al. .................... 3/1.5 |
| 4,629,459 A | | 12/1986 | Ionescu et al. |
| 4,725,274 A | | 2/1988 | Lane et al. ...................... 623/2 |
| 4,759,758 A | * | 7/1988 | Gabbay ....................... 623/2.13 |
| 5,397,348 A | * | 3/1995 | Campbell et al. .......... 623/2.38 |
| 5,549,665 A | | 8/1996 | Vesely et al. ................... 623/2 |
| 5,662,705 A | * | 9/1997 | Love et al. ..................... 623/2 |
| 5,713,950 A | | 2/1998 | Cox |
| 5,766,240 A | * | 6/1998 | Johnson ...................... 623/2.39 |
| 5,855,602 A | | 1/1999 | Angell ............................ 623/2 |
| 5,861,028 A | | 1/1999 | Angell ............................ 623/2 |
| 5,935,163 A | | 8/1999 | Gabbay ........................... 623/2 |
| 6,045,576 A | * | 4/2000 | Starr et al. .................. 623/2.41 |
| 6,074,419 A | | 6/2000 | Healy et al. |
| 6,102,944 A | | 8/2000 | Huynh et al. |
| 6,419,695 B1 | * | 7/2002 | Gabbay ..................... 623/2.36 |

OTHER PUBLICATIONS

Product Information for *Medtronic Hall Mechanical Heart Valve—Valve Function*, published at www.medtronic.com by Medtronic, Inc. (date unknown).
Product Information for *Medtronic Hall Mechanical Heart Valve—Rotatability*, published at www.medtronic.com by Medtronic, Inc. (date unknown).
Starek, Peter, et al. *Development and Clinical Experience of the Medtronic Hall Mecahnical Heart Valve*. Published by Medtronic, Inc.; 3 pages (date unknown).
Siniawski, Henryk, et al. Abstract for: *Are Stentless Aortic Valves Good Alternatives to Homografts for Valve Replacement in Active Infective Endocarditis!* (About 2001). 2 pages.
International Search Report.

* cited by examiner

*Primary Examiner*—David H. Willse
*Assistant Examiner*—Javier G. Blanco
(74) *Attorney, Agent, or Firm*—Tarolli, Sundheim, Covell & Tummino L.L.P.

(57) ABSTRACT

A system and method are disclosed for covering a mechanical heart valve with biological tissue to provide a biomechanical heart valve prosthesis. The prosthesis includes a mechanical heart valve having a moveable portion mounted within a generally annular support that permits substantially unidirectional flow of blood therethrough. One or more sheets of a biological tissue material are applied around the support heart valve to provide a sewing ring that includes the biological tissue material.

34 Claims, 7 Drawing Sheets

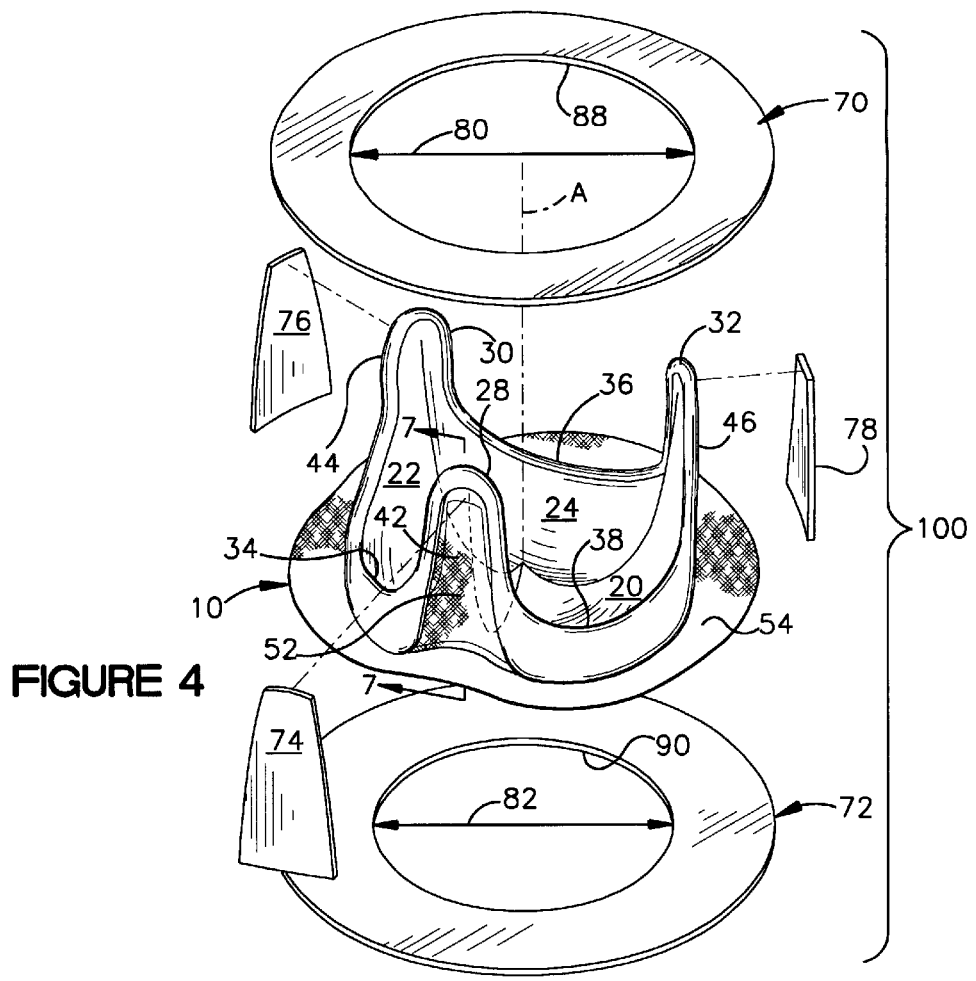
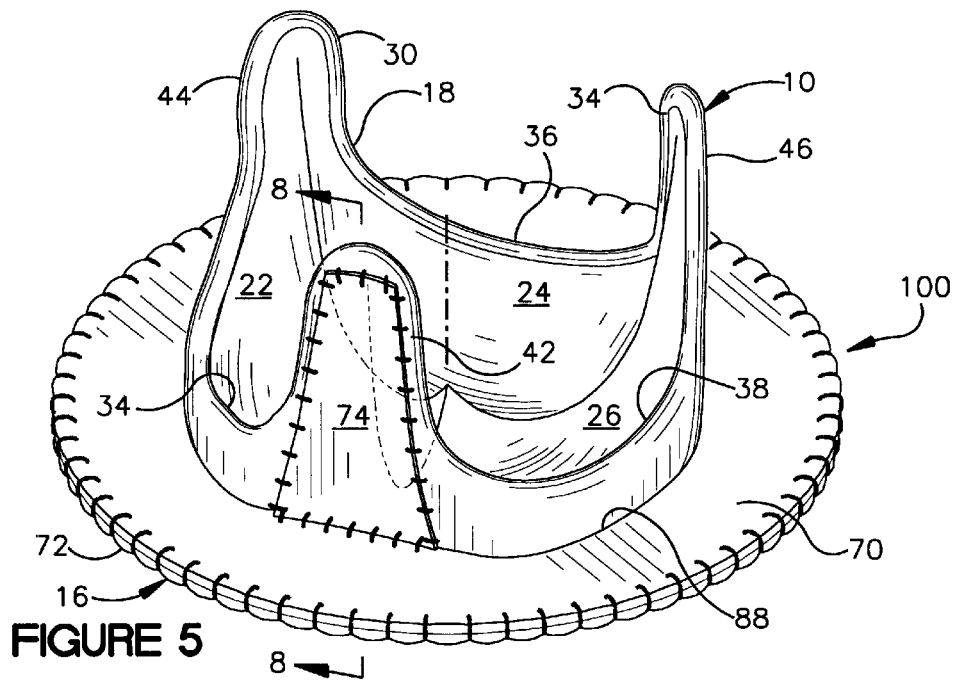

BIOMECHANICAL HEART VALVE PROSTHESIS AND METHOD FOR MAKING SAME

RELATED APPLICATION

This application is a continuation-in-part of U.S. application Ser. No. 09/563,565, which was filed May 3, 2000, and is entitled METHOD AND SYSTEM FOR PROVIDING A BIOLOGICALLY COVERED HEART VALVE PROSTHESIS.

TECHNICAL FIELD

The present invention relates to an implantable prosthetic device and, more particularly, to biomechanical heart valve prosthesis and to a method for making a biomechanical heart valve prosthesis.

BACKGROUND

It is well known to utilize mechanical heart valves and natural tissue cardiac valves to replace defective aortic and mitral valves in human patients. The decision to utilize a mechanical heart valve versus a natural tissue product often is made at the discretion of the surgeon based on personal preferences.

Common types of mechanical heart valves include ball check valves and valves having one or more moveable lens-shaped discs. The discs may be supported in cages for axial or pivotal movement within a frame structure. The mechanical valves usually are formed of titanium and/or pyrolytic carbon materials. A fabric sewing ring, such as formed of polymer or textile material, surrounds the annular frame to facilitate its implantation.

One type of natural tissue heart valve typically employs a porcine valve for implantation in a human, as they are very similar to human valves of appropriate size and generally are easy to procure. Prior art teaches the concept of removing an aortic heart valve from a pig, treating it with an appropriate fixation solution, which may include a glutaraldehyde solution, and mounting the valve into a stent.

A stent typically is formed of a resilient material, such as a plastic (e.g., DELRIN). Examples of various stent structures are disclosed in U.S. Pat. No. 3,983,581, U.S. Pat. No. 4,035,849. The stent usually is covered with a fabric material, such as DACRON, PTFE, or other suitable textile material. The fabric material provides structure for securing the valve relative to the stent. The stented heart valve prosthesis may be implanted into a patient for a heart valve replacement.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a system and method for providing a biomechanical heart valve prosthesis, which includes biological tissue, such as pericardium or collagen, associated with a mechanical heart valve. According to one aspect of the present invention the heart valve prosthesis includes a mechanical heart valve having a generally annular support and a valve member that permits substantially unidirectional flow of blood through the heart valve. For example, the mechanical valve could be a ball check valve or other valve configuration, such as having one or more moveable discs. One or more sheets of a biocompatible biological tissue material are disposed around the annular support to define at least part of a sewing ring.

In accordance with a particular aspect, the mechanical heart valve may include a fabric sewing ring. The biological tissue material thus may be applied to cover the exposed fabric material.

Another aspect of the present invention provides a method of making a heart valve prosthesis. The method includes providing a mechanical heart valve that is operative to permit substantially unidirectional flow of blood through the mechanical valve. One or more sheets of a biocompatible biological tissue material are applied around an exterior portion of the mechanical heart valve to provide a sewing ring that includes the biological tissue material. If the mechanical heart valve includes a fabric sewing ring, the biological tissue material is applied so as to cover the exposed fabric.

To the accomplishment of the foregoing and related ends, the invention, then, comprises the features hereinafter fully described and particularly pointed out in the claims. The following description and the annexed drawings set forth in detail certain illustrative aspects of the invention. These aspects are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 4 is an exploded isometric view of a heart valve prosthesis in accordance with the present invention;

FIG. 5 is an isometric view of an inflow side of heart valve prosthesis in accordance with the present invention;

DESCRIPTION OF THE INVENTION

Figure 1:
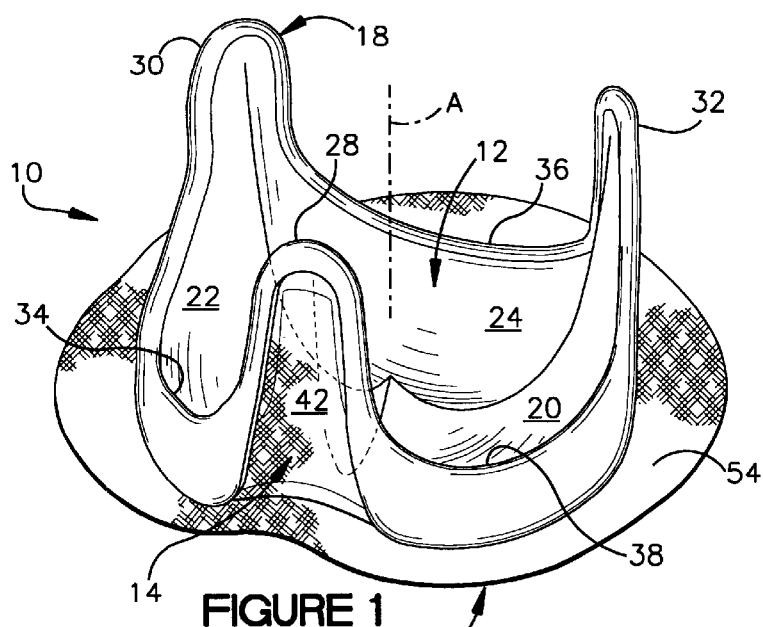
FIG. 1 is an isometric view of a heart valve mounted in a fabric-covered stent.

Various aspects of the present invention will now be described with reference to the drawings, wherein like reference numerals are used to refer to like elements throughout related views.

FIG. 1 illustrates a stented heart valve 10, which may be employed to form a biologically covered heart valve prosthesis in accordance with the present invention. The stented heart valve 10 includes a heart valve 12 mounted or attached within in a conventional stent 14. The stented heart valve 10, for example, is of the type disclosed in U.S. Pat. No. 5,861,028 or U.S. Pat. No. 5,855,602, although other valve configurations (e.g., natural tissue or mechanical valves) also may be utilized without departing from the scope of the present invention.

By way of example, the valve 12 is a natural tissue heart valve, such as a porcine heart valve, which has been trimmed and fixed in an appropriate glutaraldehyde solution. An example of a suitable fixation environment is disclosed in U.S. Pat. No. 5,861,028. The valve 12 includes an inflow end 16, an outflow end 18 and a central axis, indicated at A, extending longitudinally through the inflow and outflow ends of the valve. The valve 12 also includes a plurality of leaflets or cusps 20, 22 and 24 mounted within a generally cylindrical sidewall portion 26 (see, e.g., cross sectional view of FIGS. 7 and 8), which may be a length of valve wall extending between the inflow and outflow ends 16 and 18. The sidewall portion includes circumferentially spaced apart commissures 28, 30, and 32, which form struts at the outflow end 18 near the juncture of adjacent pair of leaflets. The heart valve 12 also has sinuses 34, 36, and 38 formed in the outflow end 18 of the valve 10 between adjacent pairs of commissures 28 and 30, 30 and 32, 32 and 28, respectively.

Figure 2:
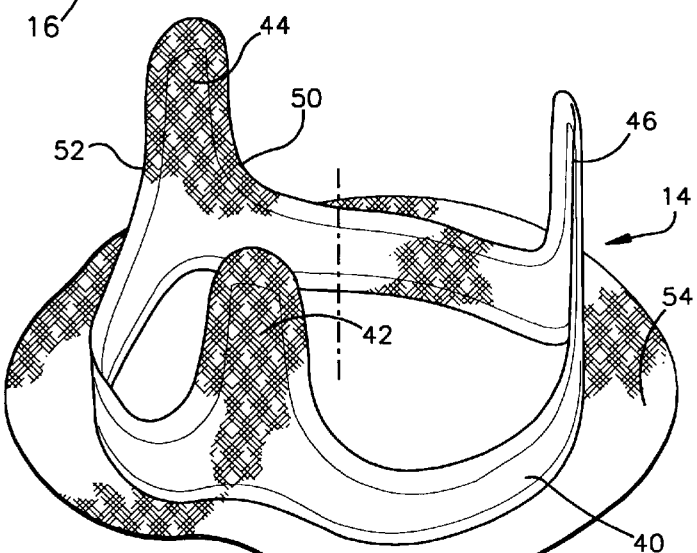
FIG. 2 is an isometric view of a fabric-covered stent.

FIG. 2 illustrates an example of the stent 14 illustrated in FIG. 1. The stent 14 includes an annular base portion 40 and elongated stent posts (or struts) 42, 44 and 46 extending from the annular base portion that correspond generally to the anatomical configuration of the heart valve 12. The stent posts 42, 44 and 46 are circumferentially spaced apart along an outflow end 50 of the base portion 40 to generally correspond to the radial positioning of the individual leaflets of the heart valve 12 (FIG. 1). The stent 14 also includes an inflow end 48 spaced axially from the outflow end 50.

The stent 14, for example, may be manufactured in various sizes and shapes by a conventional injection molding process. The stent 14 is typically formed of a thermoplastic material, such as the material known commercially as Delrin. The stent may be formed, however, of any other resilient, rigid, or flexible material according to the desired level of stiffness.

At least an exterior portion, although typically the entire stent structure 14 is covered with a nonabsorbent fabric material 52. The fabric covering is applied over and covers both the internal and external surfaces of the stent 14. By way of example, the fabric covering 52 may be an open mesh sheet of flexible material, such as a Dacron polymer cloth, a textile, or substantially equivalent material. It is to be appreciated that other fabric materials, such as plastics, synthetic materials, and the like also may be used. The fabric covering provides structure to which the valve 12 (FIG. 1) may be secured relative to the stent 14.

A generally annular implantation flange (or sewing ring) 54 may circumscribe the stent base 40 intermediate the inflow end 48 and the outflow end 50 of the stent 14. The flange 54, for example, is formed of the same material as the fabric covering 52. The flange 54 may be attached about the exterior of stent 14, such as by sewing the flange to the fabric covering 52 that surrounds the stent 14. Alternatively, the flange 54 may be formed from part of the fabric covering 52 that covers the stent 14 when the fabric covering is applied. The flange also may be ironed to form a substantially flat ring-like structure circumscribing the stent base 40. The particular positioning of the implantation flange 54 may depend upon whether the prosthesis 10 is to be implanted as a mitral valve or an aortic valve (See, e.g., U.S. Pat. No. 5,861,028). Examples of other types of stent structures that may be utilized include those disclosed in U.S. Pat. No. 3,983,581, U.S. Pat. No. 4,035,849, as well as any other stent structure known in the art.

Figure 3:
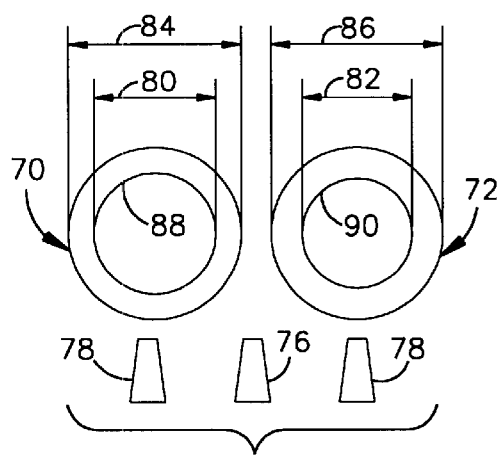
FIG. 3 is a plan view of sheets of biological material that may be employed to form a heart valve prosthesis in accordance with the present invention.

FIG. 3 illustrates a plurality of sheets 70, 72, 74, 76, and 78 of biological tissue that may be utilized, in accordance with an aspect of the present invention, to cover all fabric 52 that is exposed on a stented heart valve 12 (FIG. 1). The biological tissue, for example, is smooth animal pericardium (e.g., equine, bovine, porcine, etc.) that has been tanned or fixed in a suitable tanning environment. The tanned tissue also may be treated with heparin to improve its biocompatibility and mitigate thrombus formation.

Sheets 70 and 72 are in the form of generally annular rings, each having a respective inner diameter 80, 82 and outer diameter 84, 86. In particular, the ring 72 is dimensioned and configured for attachment to an inflow end of a stented valve 10 (FIG. 1) and, thus, has an inner diameter 82 that approximates the dimensions and configuration of the valve at the juncture between the valve and the fabric covering 52 located at the inflow end of the stented valve. The other ring 70 is dimensioned and configured to be attached to the outflow side of the implantation flange 54 (FIGS. 1 and 2). Each of the rings 70, 72 has a respective inner periphery 88, 90.

The remaining sheets 74–78 are in the form of patches that are dimensioned and configured to cover the remaining exposed fabric of the stented valve 10 (FIG. 1), namely, along the exterior of the stent posts 42–46 (FIGS. 1 and 2). While the patches are generally trapezoidal, it is to be understood and appreciated that other shapes may be used. For example, the shape of the patch may be selected according to the configuration of the stented valve and the contour of the exposed fabric material covering along the stent post and/or heart valve.

FIG. 4 is an exploded view of a heart valve prosthesis 100, in accordance with an aspect of the present invention, in which identical reference numbers are used to refer to parts previously identified with respect to FIGS. 1–3. The sheets of biological (e.g., pericardial) tissue 70–78 are aligned for attachment onto the stented valve 10, such that their visceral, or smooth, side is exposed. In particular, the ring 70 is oriented coaxially with axis A for attachment onto the inflow side of the implantation flange 54. As mentioned above, the inner diameter 80 of the ring 70 approximates (preferably slightly larger than) the outer diameter of the stented valve 10. As the ring 70 is mounted over the stent posts, the inner periphery 88 engages and circumscribes the stented valve 10 and is positioned at the juncture of the flange 54 and the stent base portion 40.

Similarly, the other ring 72 is aligned coaxially with axis A for attachment at the inflow end 16 of the stented valve 10. The inner diameter 82 is less than the outer diameter of the stented valve 10 at the inflow side juncture of the implantation flange 54 and the stent. As mentioned above, the inner diameter 82 of the ring 72 approximates the configuration of the inflow annulus of the valve 12 at the juncture of the valve and the fabric covering the stent 14. As a result, the ring 72 is able to completely cover all exposed fabric 52 at the inflow side, including the inflow side of the implantation flange 54.

The patches 74, 76, and 78 are aligned for attachment to cover exposed fabric 52 associated with each of the stent posts 42, 44, and 46, respectively. Once all the sheets are attached to the stented valve 10, no fabric material 52 is exposed. As a result, when the prosthesis 100 is implanted, there is no contact between blood and the fabric covering 52. This mitigates clot formation and infection which otherwise might occur in response to contact between blood and the fabric covering.

Figure 6:
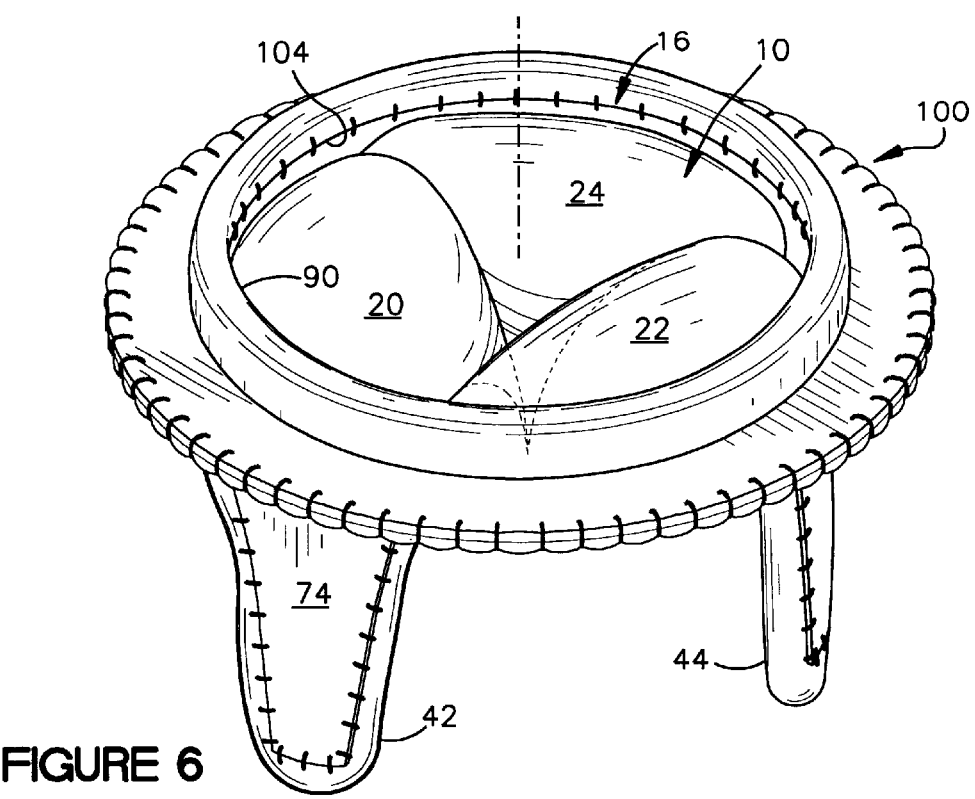
FIG. 6 is an isometric view of an outflow side of a heart valve prosthesis in accordance with the present invention.

FIGS. 5 and 6 illustrate the completed heart valve prosthesis 100 in which all exposed fabric material has been covered with biological tissue in accordance with an aspect of the present invention. In particular, FIG. 5 illustrates the prosthesis 100 as viewed from its outflow end. Each of the patches 74, 76, 78 (only patch 74 is shown) is sewn to the fabric material covering a radially outer portion of each respective stent post 42, 44, 46. The ring 70 engages and is connected to an outflow side of the implantation flange and the ring 72 engages and is connected to an inflow side of the implantation flange. The rings 70 and 72 are sewn together at an outer periphery thereof, thereby "sandwiching" the flange located between the rings. In addition or alternatively, the rings may be sewn to a perimeter to a portion of the implantation flange 54.

The inner periphery 88 of the ring 70 also is sewn to an adjacent part of the patches covering the radially outer portions the stent posts. Additional sutures (not shown) also may be employed to connect the inner periphery 88 to an outer portion of stent 14 between stent posts.

FIG. 6 illustrates the inflow end of the prosthesis 100 in which the ring 72 completely covers the fabric at the inflow end 16 of the prosthesis. The ring 72 is sewn at an inflow annulus 104 of the prosthesis 100 at the juncture of the valve 12 and the fabric-covered stent. Advantageously, the ring 72 of biological tissue conforms to the contour of at the inflow end, although additional sutures may be employed to ensure substantially tight engagement between the ring 72 and the stented heart valve 10.

Figures 7, 8:
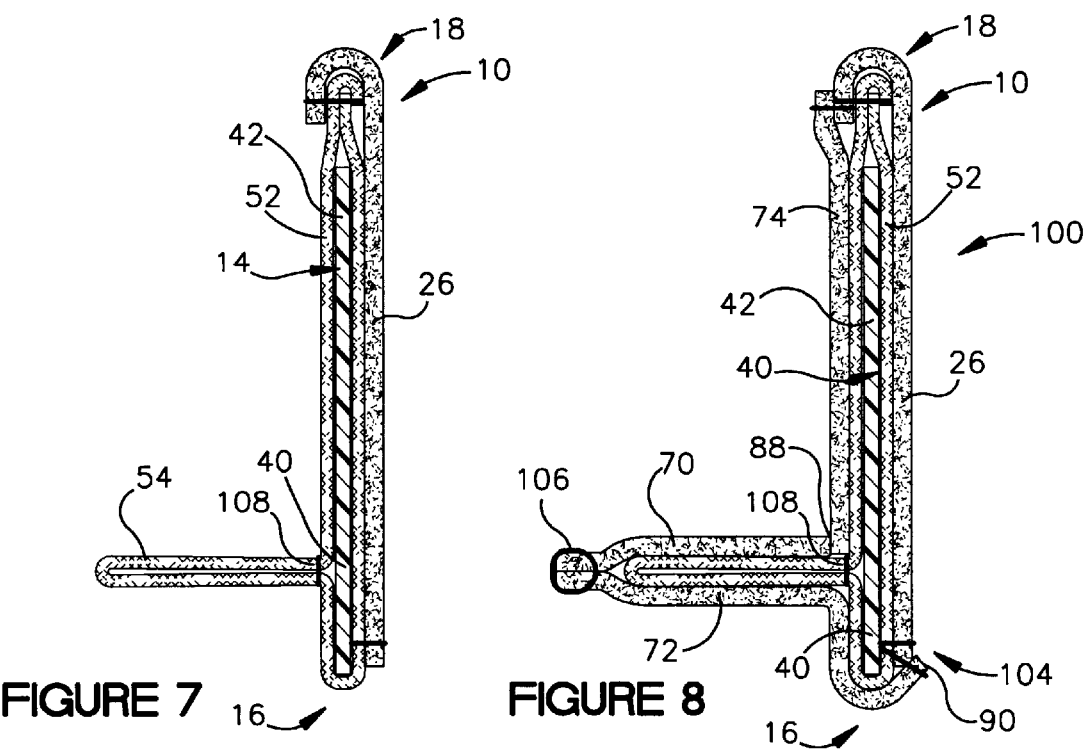
FIG. 7 is a partial side-sectional view of a stented heart valve taken along line 7—7 of FIG. 4.
FIG. 8 is a partial side sectional view of a stented heart valve taken along line 8—8 of FIG. 5.

FIGS. 7 and 8 are cross-sectional views of part of valve structures shown and described herein. It is to be appreciated that the dimensions and relative position of corresponding parts has been exaggerated for purposes of clarity of illustration.

Referring to FIG. 7, a cross-sectional view of part of the stented heart valve of FIG. 4, taken along line 7—7, is illustrated. This further illustrates the fabric covering 52 that surrounds the stent 14. In addition, the implantation flange 54 is illustrated as being spaced from the inflow end 16 of the valve 10. A suture 108 may be employed to maintain the flange in a desire substantially flat configuration. As mentioned above, the relative axial placement of the implantation flange 54 on the stent 14 may vary according to whether the prosthesis is to be used for mitral or atrioventricular valve replacement, and all such positions are within the scope of the present invention. Moreover, the system and method, in accordance with an aspect of the present invention, also may be employed with a stent or stented valve having no implantation flange.

FIG. 8 is another cross-sectional view of part of the heart valve prosthesis 100 of FIG. 5, taken along line 8—8, in accordance with an aspect of the present invention. The rings 70 and 72 sandwich the implantation flange 54 and are connected together along the periphery of the rings and flange by appropriate sutures 106. As mentioned above, the sutures 106 alternatively may connect the rings 70 and 72 to the flange 54. The inner periphery 88, 90 of each ring 70, 72 also is sewn to a corresponding portion of the stented valve 10. In particular, the inner periphery 88 of the ring 70 is sewn to the patches (e.g., 74) and also may be connected to the underlying fabric covering 52 circumscribing the stented valve 10. The inner periphery of the ring 72 is sewn to the inflow annulus 104 of the prosthesis 100 so as to cover all fabric covering at the inflow portion of the stented valve. The biological tissue patch 74 also is sewn to cover the exposed portion of the fabric material associated with the stent post 42 (see, e.g., FIG. 5).

Figure 9:
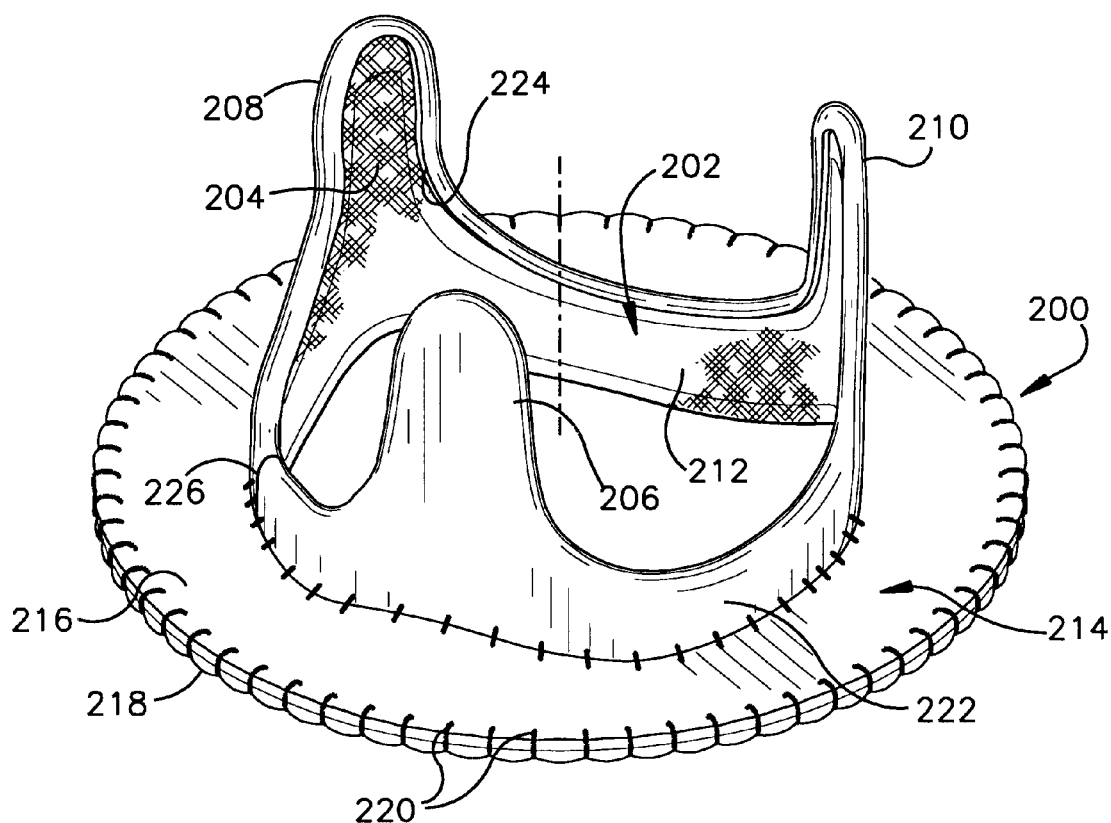
FIG. 9 is an isometric view of fabric-covered stent that is covered with biological tissue material in accordance with the present invention.

FIG. 9 is an example of a stent 200 that has been covered with biological tissue in accordance with an aspect of the present invention. The stent 200 includes a stent member 202 that has been covered with a fabric material 204, such as shown and described with respect to FIG. 2. The stent 200 also includes stent posts 206, 208, and 210 extending substantially coaxially from a stent base portion 212 in a circumferentially spaced apart relationship.

Biological material has been applied to a the fabric-covered stent member 202 in accordance with an aspect of the present invention. In particular, the stent 200 includes an implantation flange 214 formed of a two layers 216 and 218 of biological tissue (e.g., animal pericardium). Each of the layers 216,218, for example, is in the form of a ring-like sheet of animal pericardium, such as sheets 70 and 72 shown and described hereinabove. The outer periphery of each of the layer is sewn together via sutures 220. The radially inner portion of each of the layers 216, 218 also is sewn the fabric covering 204.

A layer 222 of biological tissue also covers the fabric material 204 covering the radially outer extent of the stent 200. This layer 222 may be in the form of a single sheet of animal pericardium that circumscribes the fabric-covered stent 200. As illustrated in the example of FIG. 9, the layer 222 may be trimmed to conform to the contour of the stent posts 206–210 along a outflow end of the stent. The layer also may cover the fabric material 204 at an outflow margin 224 of the stent member 202 so as to mitigate abrasion that may occur upon contact between leaflets and the outflow rails. Because the layer 220 typically is formed of an elongated sheet of the biological tissue, a butt seam 226 is exposed. The butt seam 226 of the sheet 222 may be positioned intermediate stent posts 206 and 208, with two ends of the layer 222 seamed together end-to-end with substantially no overlap to define the seam.

It is to be appreciated that the layer 220 may be applied to the stent 200 before or after formation of the implantation flange 214. For example, if the stent 200 does not include a fabric implantation flange (as shown in FIG. 2), then the layer 220 may cover the entire radially outer portion of the stent member 202. A double layer (layers 216 and 218) biological material may then be configured to form the implantation flange 214, with the inner portion of each layer 210, 212 being secured to the stent outer layer 222 and/or to the underlying fabric covering 204. In contrast, if the stent 200 includes a fabric implantation flange, then the layer 222 may circumscribe an outflow portion of the stent 200, such as from the juncture of the flange to the outflow end of the stent 200.

While in the example of FIG. 9, the radially inner portion of the stent exposes some fabric material 214 (other than at the outflow margin 224), it is to be appreciated that the inner portion also may be covered with a biological material, such as animal pericardium. However, a heart valve mounted within the stent 200 usually will completely cover the interior exposed portions of the fabric material.

Figure 10:
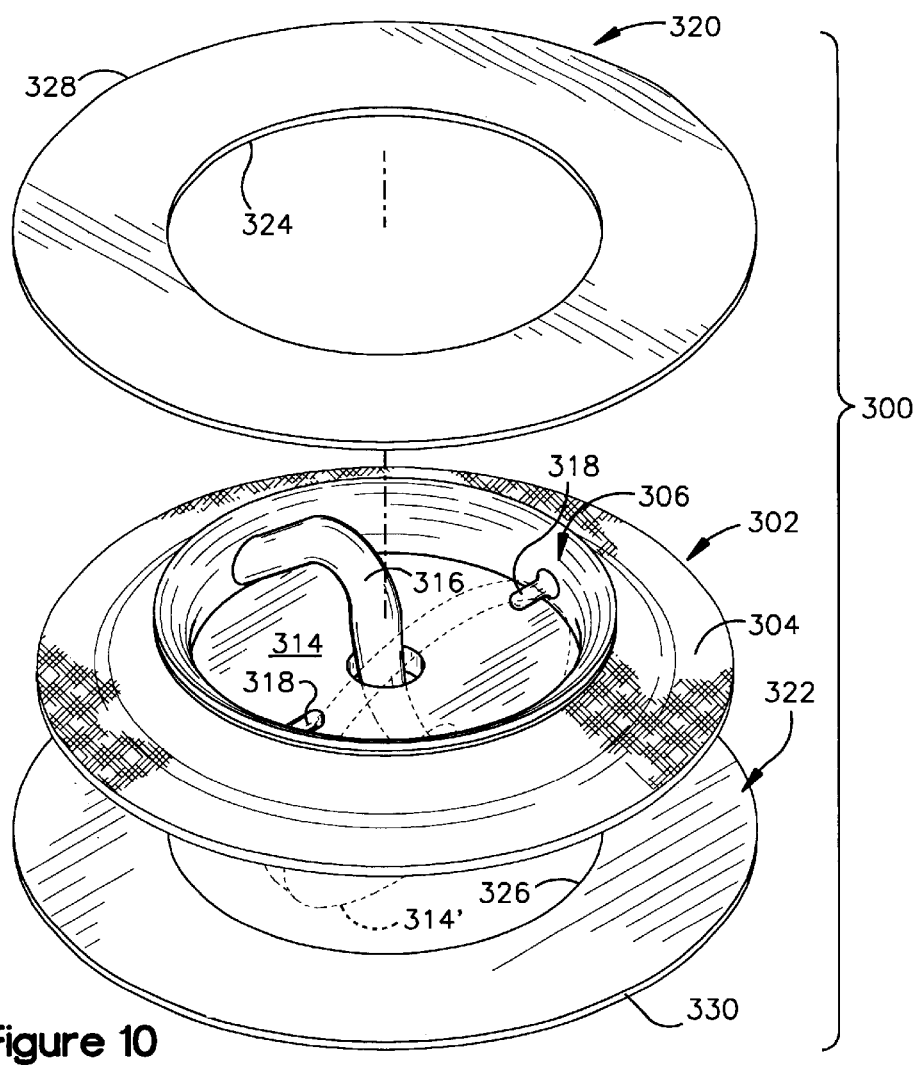
FIG. 10 is a partially exploded view of an example of a biomechanical heart valve prosthesis in accordance with the present invention.
Figure 11:
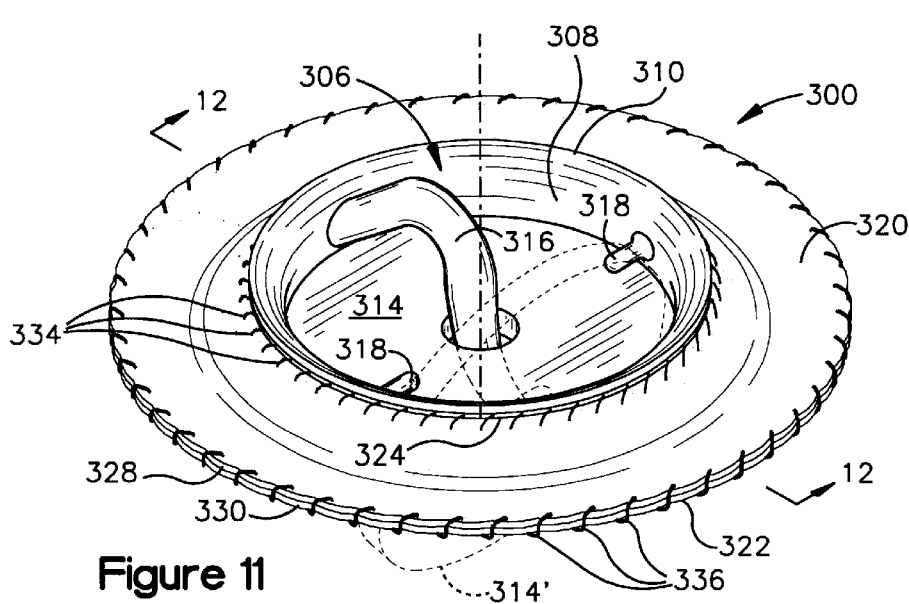
FIG. 11 is a view of a biomechanical heart valve prosthesis in accordance with the present invention.
Figure 12:
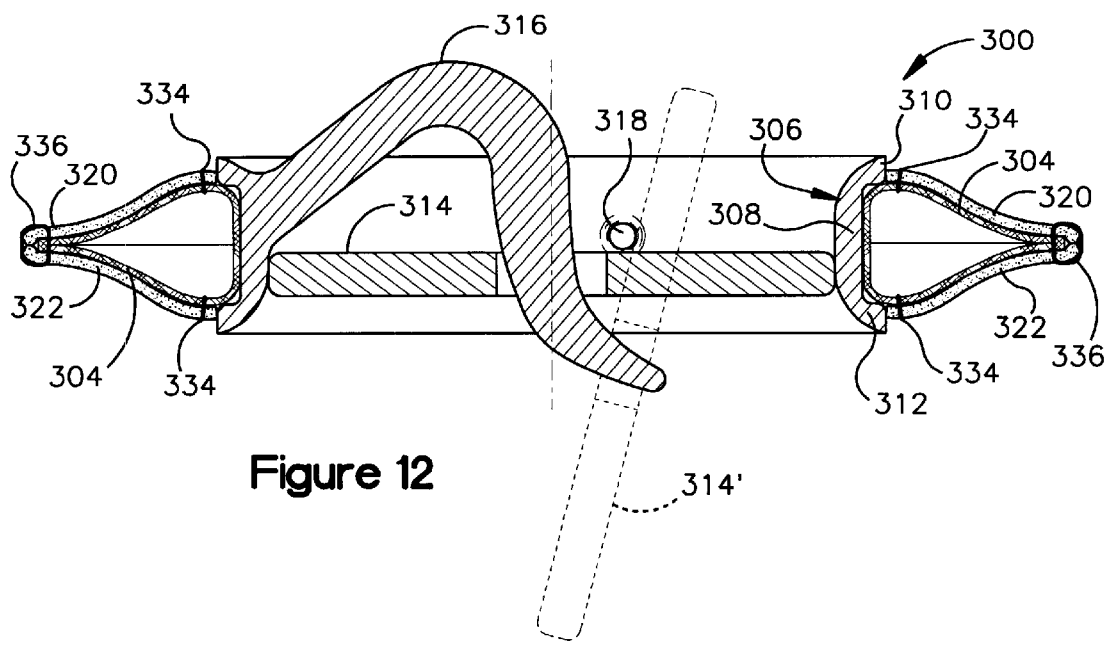
FIG. 12 is a cross-sectional view of the biomechanical heart valve prosthesis taken along line 12—12 of FIG. 11.

FIGS. 10–12 illustrate an example of a biomechanical heart valve prosthesis 300 in accordance with an aspect of the present invention. FIG. 10 depicts a partially exploded view of the prosthesis 300. The prosthesis 300 includes a mechanical heart valve 302 having an associated sewing ring 304, which is mounted coaxially around the valve. The heart valve 302 also includes a generally annular base portion or annulus 306, which is formed of a generally rigid material, such as pyrolytic carbon, a biocompatible plastic or metal material, and the like.

As best shown in FIG. 12, the annulus 306 includes a generally cylindrical portion 308 that extends axially between spaced apart end portions 310 and 312. The end portions 310 and 312 of the annulus 306 define flange portions that extend radially outwardly relative to the intermediate cylindrical portion 308. The flange portions at the ends 310 and 312 help retain the fabric sewing ring 304 at a desired axial position between the ends when positioned around the valve 302. The sewing ring 304 thus is mounted over and circumscribes an exterior part of the cylindrical portion 308 of the annulus 306. An interior portion of the fabric sewing ring could be provided with additional fabric material, cloth or other material to increase stiffness and/or provide a desired shape and contour of the fabric sewing ring.

The mechanical heart valve 302 also includes a valve portion 314 operative to permit substantially unidirectional flow of blood through the mechanical heart valve 302. By way of example, the valve portion 314 is moveable between an open condition (illustrated in phantom at 314') and a closed condition. The valve portion 314 is illustrated as a generally circular disc supported relative to the annulus 306 by a curved arm 316, which extends from the annulus through a central aperture of the valve portion. The valve portion 314 is moveable relative to (e.g., along) the arm 316 and annulus 306 between open and closed conditions. The exemplary mechanical heart valve 302 further includes fingers 318 that extend radially inwardly from the cylindrical portion 306. The fingers 318 cooperate with the pivot arm 316 to limit movement of the valve portion 314 between its open and closed conditions.

Those skilled in the art will understand and appreciate that other types and configurations of mechanical heart valves (e.g., ball-check heart valves, etc.) may be utilized in accordance with an aspect of the present invention. Examples of mechanical heart valves that may be utilized in accordance with an aspect of the present invention are commercially available from various manufacturers and associated distributors, such as, including Medtronic, Inc., Omniscience, Inc., St. Jude Medical, and others.

In accordance with an aspect of the present invention, the biomechanical heart valve prosthesis 300 includes one or more sheets 320 and 322 of a biocompatible, biological tissue material. In the example of FIG. 10, two annular flat sheets 320 and 322 of the tissue material are illustrated in an axially exploded position at opposite sides of the heart valve 302. Each of the rings 320 and 322 includes an inner circular edge portion 324, 326 and an outer edge portion 328 and 330 spaced radially from each respective inner edges. The inner edges 324 and 326 are dimensioned and configured to have a diameter that approximates an outer diameter of the cylindrical portion 308 of the annulus 306. The rings 320 and 322 are employed to cover at least exposed fabric material of the mechanical heart valve.

By way of illustration, the rings 320 and 322 are formed from one or more sheets of a natural tissue material, such as animal pericardium (e.g., bovine, equine, porcine, human, etc.). The natural tissue material may be chemically treated in a suitable fixation solution, such as including glutaraldehyde. By way of further illustration, the rings 320 and 322 may be formed from a NO-REACT® patch, which is commercially available from Shelhigh, Inc., of Millburn, N.J. The NO-REACT® patch helps improve the biocompatibility of the resulting prosthesis 300, as shown in FIGS. 11 and 12, thereby mitigating the likelihood of a patient rejecting an implanted prosthesis. The NO-REACT® pericardial patch also resists calcification.

It is to be understood and appreciated that other types of biocompatible materials (e.g., any biological tissue, collagen, as well as other natural tissue or synthetic materials) also could be utilized to cover the exposed fabric material and provide a biomechanical heart valve prosthesis 300 in accordance with the present invention. Therefore, by combining the treated natural tissue ring or rings 320, 322 with a mechanical heart valve 300, in accordance with an aspect of the present invention, the likelihood of infection after implantation of the prosthesis may be mitigated.

As shown in FIGS. 11 and 12, each of the rings 320, 322 is positioned near a respective end portion 310, 312 of the mechanical heart valve 302, such that its inner edge 324, 326 engages a juncture of the associated end portion and the sewing ring 304. For example, sutures 334 secure the inner edges 324 and 326 relative to an adjacent part of the sewing ring 304 near the respective end portions 310, 312.

Intermediate portions of the rings 320 and 322 extend from the sutures 334 and, in turn, cover the fabric sewing ring 304. That is, the outer edge portions 328 and 330 of the respective rings 320 and 322 extend radially outwardly from the annulus 306 to a position beyond an outer extent of the fabric sewing ring 304. The biocompatible rings 320 and 322 thus sandwich the fabric sewing ring 304.

The outer edge portions 328 and 330 of the respective rings 320 and 322 are sewn together, such as by sutures 336, to define a radial outer extent of the biologically covered sewing ring. The sutures 336 also may extend through a radially outer portion of the fabric sewing ring 304, as shown in FIG. 12, to help anchor the rings 320 and 322 to the heart valve 302. As a result, the combination of the rings 320 and 322 and an exterior portion of the annulus 306 completely enclose the fabric sewing ring 304, such that no remaining fabric material is exposed.

Additional sutures and/or surgical adhesive materials (not shown) could be employed to help the rings 320 and 322 conform to the contour of the particular fabric sewing ring 304.

In certain circumstances, it may be desirable to omit a fabric material sewing ring from a mechanical heart valve.

FIGS. 13–16 illustrate another biomechanical heart valve prosthesis 368, in accordance with an aspect of the present invention, having no fabric sewing ring.

Figure 13:
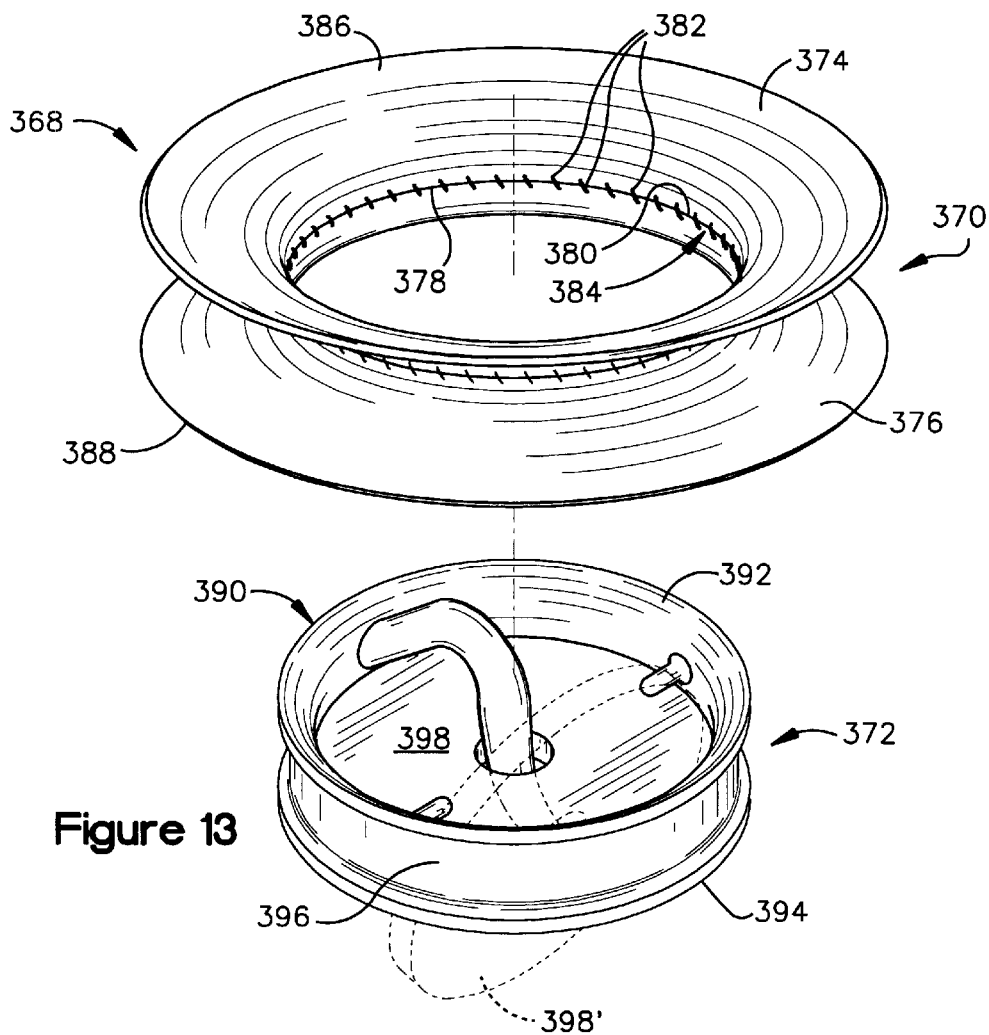
FIG. 13 is an exploded view of a biomechanical heart valve prosthesis in accordance with the present invention.

FIG. 13 depicts an exploded view of the prosthesis 368, such as, for example, at an early stage of manufacture. The prosthesis 368 includes a sewing ring 370 of one or more sheets of a treated biocompatible biological tissue material and a mechanical heart valve 372. The biological tissue material may be substantially identical to that shown and described with respect to FIGS. 10–12.

In accordance with one aspect of the present invention, the sewing ring 370 is formed of a pair of annular rings 374 and 376. The rings 374 and 376 may be substantially identical in size and shape, although differently configured rings also could be used in accordance with the present invention. Each of the rings 374,376 includes a substantially circular inner edge 378, 380, which edges are sewn together by sutures 382 to define an inner portion 384 of the combined annular structure.

Figure 14:
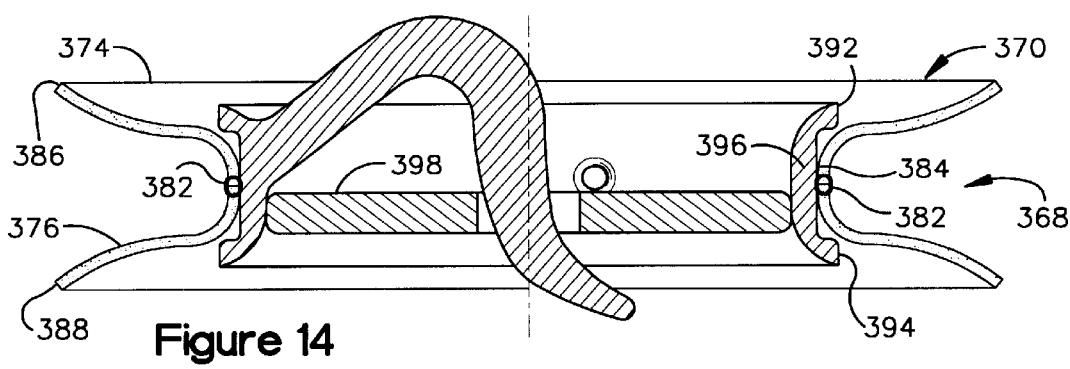
FIG. 14 is a cross-sectional view of a biomechanical heart valve prosthesis, in accordance with the present invention, illustrating the prosthesis at an intermediate stage of manufacture.

The rings 374 and 376 also include outer edges 386 and 388 spaced radially outwardly from the inner edges 374 and 376, respectively. The outer edges 386 and 388, for example, may be urged generally away from the inner portion 384 of the rings 374 and 376 to provide a C-shaped cross-sectional configuration, such as shown in FIGS. 13 and 14. The inner portion 384 of the sewing ring 370, for example, has an inner diameter that generally approximates or is slightly less than the outer diameter of the mechanical heart valve 372, around which the ring is mounted, as shown in FIG. 14.

While FIG. 14 illustrates the biological sewing ring 370 positioned around the heart valve 372 at an intermediate manufacturing stage, it is appreciated that such configuration could be utilized to provide a pair of sewing rings to implant a mechanical heart valve in accordance with the present invention.

As another possible alternative, for example, the ring 370 could be formed of a single sheet of an elongated biological tissue material, with ends of the sheet being connected end to end to form a cylindrical ring. Such alternative construction of the ring further includes side portions, which may be urged radially outwardly away from the inner portion 384 to provide the C-shaped cross-section, as shown in FIG. 14.

Referring back to FIG. 13, the heart valve 372 includes an annular support 390 having ends 392 and 394 that are spaced apart from each other by an intermediate, short cylindrical portion 396 of the support. A valve portion 398 is mounted within the annulus of valve 372 to permit substantially unidirectional flow of blood through the valve. For example, the valve portion 398 is moveable relative to the annular support 390 between an open condition (illustrated in phantom at 398') and its closed condition.

Because the mechanical heart valve 372 in the example of FIGS. 13–16 is substantially similar to the valve shown and described with respect to FIGS. 10–12, further description of the valve and its operation has been omitted for sake of brevity. It is to be appreciated that other mechanical heart valve configurations different from that shown herein could be utilized in accordance with an aspect of the present invention (e.g., ball check valves, valves with multiple moving valve members, valve members fixed to pivot arms, etc.).

As mentioned above, FIG. 14 depicts the C-shaped ring 370 mounted around the annular support 390 exterior of the heart valve 372 according to an aspect of the present invention. The inner portion 384 of the ring 370, for example, engages and circumscribes an external part of the cylindrical portion 396 of the valve 372. Accordingly, the flange portions at the ends 392 and 394 of the valve 372 help hold the biological sewing ring 370 between the ends.

Figure 15:
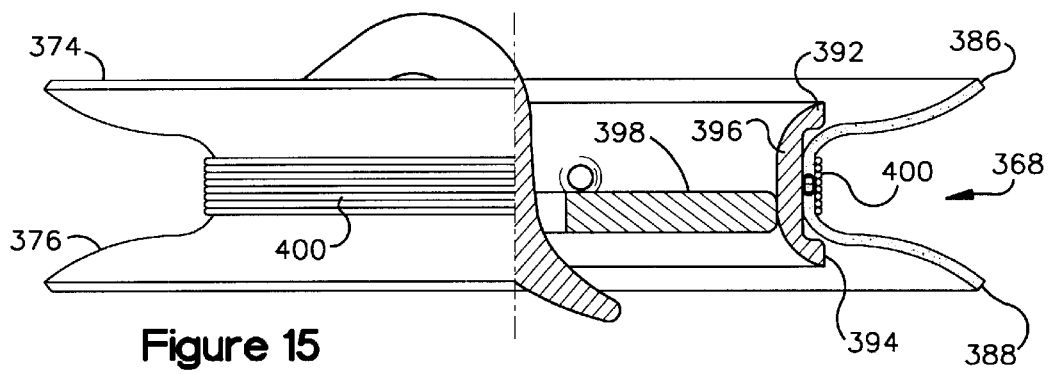
FIG. 15 is a partial cross-sectional view of a biomechanical heart valve prosthesis, in accordance with the present invention, illustrating the prosthesis at another stage of manufacture.

With reference to FIG. 15, to further inhibit movement of the ring 370 relative to the heart valve 372, one or more retaining features 400 may be applied to the inner portion 384 of the ring 370 to hold the ring in engagement with the generally rigid cylindrical portion 396 of the valve 372. In accordance with a particular aspect of the present invention, the retaining feature 400 includes one or more sutures that extend circumferentially around the inner portion 384 of the ring 370 and the cylindrical portion 378 of the heart valve 372, such as shown in FIG. 15.

By way of illustration, as shown in FIG. 15, the retaining feature 400 includes a plurality of windings of a relatively thick sterile suture material applied around the ring 370 and the cylindrical portion 378. Such windings of the retaining feature 400 may be overlapping or non-overlapping between the ends 376 and 378 of the valve 372. As a result of wrapping the sutures around the biological ring 370 and mechanical heart valve 372 for several turns, the attachment of the ring to the valve is improved.

Those skilled in the art will understand and appreciate various types of retaining features 400 that could be utilized to hold the inner portion 384 of the ring 370 against the cylindrical portion 378 of the valve 372. By way of example, instead of sutures, one or more rings of suitable biocompatible material, such as biological tissue, fabric, synthetic materials, etc., may be applied around the ring 370 and the annular support 390 of the valve 372. In addition, valve 372 itself could be reconfigured to permit sutures or other means to be applied through part of the valve to anchor the biological ring 370 relative to the valve.

Figure 16:
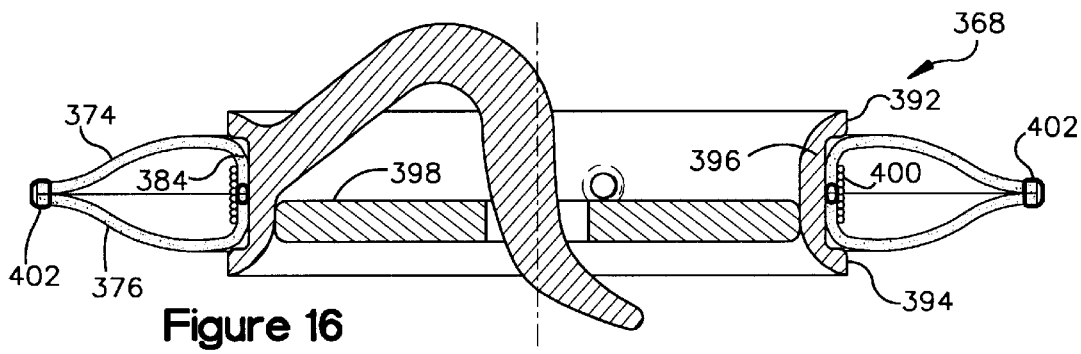
FIG. 16 is a cross-sectional view of a biomechanical heart valve prosthesis in accordance with the present invention.

FIG. 16 illustrates the heart valve prosthesis 368, which may be formed from the structure shown in FIG. 15, in accordance with an aspect of the present invention. The resulting prosthesis 368, for example, may be produced from the structure illustrated in FIG. 15 by connecting the outer edge portions 386 and 388 to each other, such as by sutures 402. In particular, the outer edges 386 and 388 of the annular rings 374 and 376 are sewn together, such that the rings collectively form a generally tubular ring structure that encloses the retaining sutures 400. In addition, the outer edges 386 and 388 of the rings 374 and 376 define a radially outer extent of the biomechanical heart valve prosthesis 368.

Figure 17:
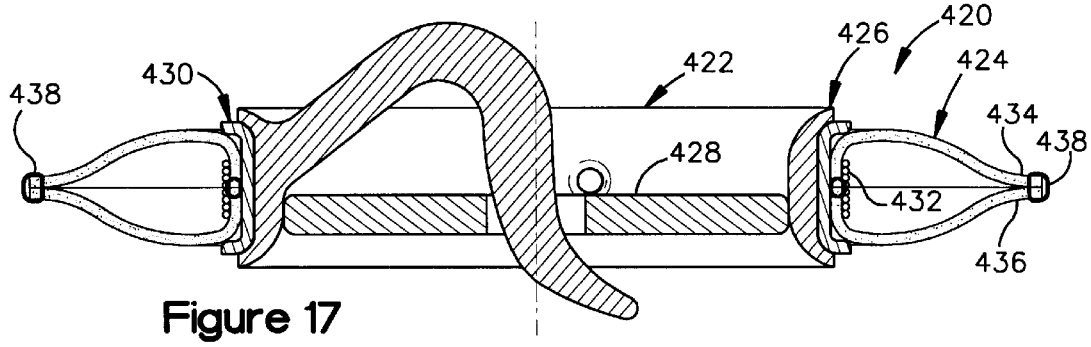
FIG. 17 is an example of another biomechanical heart valve prosthesis, in accordance with the present invention, illustrating an additional ring to facilitate rotation of part of a mechanical heart valve.

FIG. 17 illustrates another example of a biomechanical heart valve prosthesis 420 in accordance with an aspect of the present invention. The prosthesis 420 includes a mechanical heart valve 422 and a ring 424 of a biological tissue material that covers an exterior portion of the heart valve in accordance with an aspect of the present invention.

In this example, the mechanical heart valve 422 is substantially similar to the examples of FIGS. 10–16 and, thus, further description of the mechanical heart valve and its operation has been omitted for sake of brevity. Briefly stated, the mechanical heart valve 422 includes an inner annular support 426 to which a valve portion (e.g., a disc) 428 is moveably mounted to permit substantially unidirectional flow of blood through the valve. In addition, the mechanical heart valve 422 includes an outer ring 430 mounted around the annular support 426 to permit rotation of the annular support and associated valve portion 428 relative to the outer ring. The outer ring 430 thus defines an outer annulus of the mechanical heart valve 422. By way of illustration, the outer ring 430 is useful during implantation of the prosthesis 420 to rotate the support 426 and the valve portion 428 at a desired angular orientation relative to the heart.

The biological tissue ring 424 is positioned around the outer ring 430 to define a biological tissue sewing ring to facilitate implantation of the prosthesis 420. In accordance with one aspect, the biological ring 424 defines a tubular ring having an interior in which a retaining feature 432 (e.g., one or more sutures) holds the biological ring against an exterior surface of the outer ring 430. Radially outer edges 434 and 436 of the sewing ring 424 are connected together (e.g., by sutures 438) to provide a tubular ring configuration, as shown in FIG. 17.

Alternatively, if the mechanical heart valve 422 includes a fabric sewing ring, similar to the example of FIGS. 10–12, the biological tissue material may be applied to cover the exposed fabric material of sewing ring. The sewing ring, for example, would circumscribe the outer ring 430. As a result, during implantation, the inner support ring 426 and associated valve 428 may be rotated relative to the outer ring 430 and the biological sewing ring. Those skilled in the art will understand and appreciate various other configurations of mechanical heart valves that may be implemented in accordance with an aspect of the present invention.

In certain circumstances, it may be desirable to store in a dry condition a biological tissue sewing ring and/or a mechanical heart valve prosthesis having a sewing ring that includes biological tissue in accordance with an aspect of the present invention. It further may be desirable to keep the biological tissue material generally soft and pliable to facilitate its implantation.

In order to provide a pliable biological ring, in accordance with an aspect of the present invention, the biological tissue may be immersed in a sterile solution of glycerin, such as after an appropriate fixation treatment and/or detoxification. By way of further illustration, the biological tissue material may be immersed in a solution having about 2% to about 25% glycerin for a time period of about one to about five hours. After such treatment, the biological tissue material of the biomechanical heart valve may be removed from the solution and dried, such that its moisture is removed. Advantageously, some of the glycerin penetrates the tissue and remains in the tissue so as to maintain the tissue in a pliable condition, even after being dried.

It is to be appreciated that the immersion of the tissue in the glycerin solution may occur before attachment of the tissue to the mechanical heart valve. In addition or alternatively, the immersion into the glycerin solution may be performed while the tissue is attached to the mechanical heart valve in accordance with an aspect of the present invention. Those skilled in the art will understand and appreciate other suitable solutions that may be utilized to help maintain the biological tissue material in a pliable condition even after it has been dried.

In view of the foregoing structures and methodology, it will be appreciated by those skilled in the art that a system and method implemented according to the present invention help reduce a possible source of infection after the valve is implanted. In particular, a prosthesis implemented in accordance with the present invention, mitigates contact between fabric material (e.g., polymer materials, such as PTFE, or textiles) and blood. Once infection mounts in fabric material, it is practically impossible to eradicate. As a result, the patient may require re-operation, which exposes the patient to additional risk that has a relatively high mortality rate. The fabric material, if left exposed to blood, also provides a site that is prone to clot formation, which may result in other complications for the patient. As a result, the present invention provides a heart valve prosthesis that mitigates clot formation as well as helps reduce the incidence of infection. The biological material covering also tends to improve the compatibility between the heart valve prosthesis and the valve recipient.

What has been described above are examples of the present invention. It is, of course, not possible to describe every conceivable combination of components or methodologies for purposes of describing the present invention, but one of ordinary skill in the art will recognize that many further combinations and permutations of the present invention are possible. For example, various types of heart valves, which may be different from those shown and described herein (e.g., ball check mechanical valves, etc.), can benefit from applying biological tissue around such valves in accordance with an aspect of the present invention. Accordingly, the present invention is intended to embrace all such alterations, modifications and variations that fall within the spirit and scope of the appended claims.

What is claimed is:

1. A heart valve prosthesis, comprising:
   a mechanical heart valve having a generally annular support, the mechanical heart valve being operative to permit substantially unidirectional flow of blood through the mechanical heart valve; and
   biocompatible biological tissue material disposed around the annular support to define at least part of a sewing ring.

2. The heart valve prosthesis of claim 1, further comprising a retaining feature that holds the tissue material at a desired position relative to the annular support.

3. The heart valve prosthesis of claim 2, wherein the retaining feature further comprises at least one suture that holds the tissue material at the desired position relative to the annular support.

4. The heart valve prosthesis of claim 1, wherein the sewing ring further comprises a generally tubular ring of the biological tissue material that circumscribes the annular support, the generally tubular ring having a radially inner portion that engages an exterior portion of the mechanical heart valve and a radially outer portion that extends from the radially inner portion.

5. The heart valve prosthesis of claim 4, further comprising a retaining feature located within an interior of the generally tubular ring, the retaining feature urging the radially inner portion of the generally tubular ring into engagement with the exterior portion of the mechanical heart valve.

6. The heart valve prosthesis of claim 5, wherein the retaining feature further comprises a plurality of windings of at least one suture that circumscribe the radially inner portion of the generally tubular ring and the exterior portion of the mechanical heart valve.

7. The heart valve prosthesis of claim 4, wherein the generally tubular ring further comprises a pair of annular sheets of the tissue material, each of the annular sheets having a radially inner edge portion and an outer portion spaced outwardly from the respective inner edge portion, the annular sheets being connected together near the respective inner portions and near the respective outer portions to define the generally tubular ring.

8. The heart valve prosthesis of claim 7, further comprising a retaining feature located within an interior of the generally tubular ring, the retaining feature urging a radially inner portion of the generally tubular ring into engagement with the exterior portion of the mechanical heart valve.

9. The heart valve prosthesis of claim 1, wherein the tissue material further comprises at least one of a treated animal pericardium and collagen.

10. The heart valve prosthesis of claim 1, further comprising a fabric material disposed around the annular support to define a fabric sewing ring of the mechanical heart valve, the tissue material being disposed around the annular support and the fabric sewing ring so as to cover externally exposed fabric material.

11. The heart valve prosthesis of claim 10, wherein the biological tissue material further comprises a pair of annular sheets of the biocompatible biological tissue material, each of the annular sheets having a radially inner portion and a radially outer portion, the radially outer portions being connected together to define a radially outer extent of the heart valve prosthesis, the radially inner portions being connected to generally axially opposed portions of the fabric sewing ring.

12. The heart valve prosthesis of claim 1, further comprising glycerin within the biological tissue material so as to render the tissue generally pliable when stored in a dry condition.

13. A heart valve prosthesis, comprising:
a mechanical heart valve having an annulus and a moveable part supported within the annulus to permit generally unidirectional flow of blood through the mechanical heart valve;
at least one sheet of a treated biological tissue material circumscribing at least part of an exterior portion of the mechanical heart valve;
at least one retaining element operative to attach a radially inner portion of the at least one sheet of a treated biological tissue about the exterior portion of the mechanical heart valve.

14. The heart valve prosthesis of claim 13, wherein the retaining element further comprises at least one suture that extends generally circumferentially around the radially inner portion of the at least one sheet and the exterior portion of the mechanical heart valve to maintain engagement therebetween.

15. The heart valve prosthesis of claim 13, wherein the at least one sheet further comprises a generally tubular ring of the biological tissue material that circumscribes the mechanical heart valve, the retaining element being located within the tubular ring.

16. The heart valve prosthesis of claim 13, wherein the biological tissue material further comprises at least one of treated animal pericardium and collagen.

17. The heart valve prosthesis of claim 16, further comprising glycerin in the biological tissue material to render the biological tissue material generally pliable.

18. A heart valve prosthesis, comprising:
a mechanical heart valve having an annular support and a valve member supported within the annular support to permit generally unidirectional flow of blood through the mechanical heart valve;
a sewing ring of a fabric material disposed around the annular support to form a fabric sewing ring; and
at least one sheet of a biocompatible biological tissue material covering externally exposed portions of the fabric material.

19. The heart valve prosthesis of claim 18, wherein the biological tissue material further comprises a pair of annular sheets of the biocompatible biological tissue material, each of the annular sheets having a radially inner portion and a radially outer portion, the radially outer portions being connected together to define a radially outer extent of the heart valve prosthesis, the radially inner portions being connected to generally axially opposed portions of the fabric sewing ring so that exposed portions of the fabric material are covered.

20. The heart valve prosthesis of claim 18, further comprising glycerin within the biological tissue material so as to render the biological tissue material generally pliable.

21. The heart valve prosthesis of claim 18, wherein the biological tissue material further comprises at least one of treated animal pericardium and collagen.

22. A heart valve prosthesis, comprising:
mechanical valve means for permitting substantially unidirectional flow of blood through an annulus thereof;
treated, biocompatible biological tissue means for covering around the annulus of the valve means and for providing a sewing ring to facilitate implantation of the prosthesis; and
means for retaining the biocompatible biological tissue means around the valve means.

23. The heart valve prosthesis of claim 22, further comprising fabric means mounted circumferentially around the annulus of the valve means, the biological tissue means covering externally exposed portions of the fabric means.

24. The heart valve prosthesis of claim 23, wherein the tissue means further comprises a pair of annular means for, when connected around the valve means, forming a biological cover over exposed portions of the fabric means.

25. A method of making a biomechanical heart valve prosthesis, comprising:
providing a mechanical heart valve operative to permit substantially unidirectional flow of blood through the mechanical heart valve; and
applying at least one sheet of a biocompatible biological tissue material around an exterior portion of the mechanical heart valve to provide a sewing ring that includes the biological tissue material.

26. The method of claim 25, wherein the mechanical heart valve further includes a sewing ring of a fabric material, the at least one sheet being applied to cover exposed fabric material of the sewing ring.

27. The method of claim 25, further comprising applying a pair of annular sheets of the biological tissue material around the mechanical heart valve, at least radially outer edge portions of the pair of annular sheets being connected together to define a radially outer extent of the sewing ring.

28. The method of claim 27, further comprising connecting together radially inner portions of the pair of annular sheets to form the generally tubular ring that circumscribes the mechanical heart valve.

29. The method of claim 28, wherein, prior to connecting the radially outer portions of the pair of annular sheets together, the method further comprises securing a radially inner portion of an annular member formed of the pair of annular sheets about an exterior portion of the mechanical heart valve.

30. The method of claim 27, wherein the mechanical heart valve further comprises a fabric sewing ring of a fabric material mounted about the exterior portion of the mechanical heart valve, the radially inner portion of each of the pair of annular sheets being connected to generally axially opposed portions of the fabric sewing ring, such that exposed fabric material is covered by the pair of annular sheets.

31. The method of claim 25, further comprising immersing the biological tissue material in a glycerin solution.

32. The method of claim 31, further comprising removing moisture from the biological tissue material and storing the heart valve prosthesis in a substantially dry condition, such that some of the glycerin remains in the biological tissue material to render the biological tissue material generally pliable.

33. The method of claim 25, wherein the biological tissue material further comprises at least one of a treated animal pericardium and collagen.

34. A heart valve prosthesis, comprising:

a generally annular support;

a heart valve mounted within the support to permit substantially unidirectional flow of blood through the heart valve;

at least one sheet of biocompatible biological tissue material mounted around and covering the annular support, one part of the at least one sheet of biocompatible biological tissue material defining a sewing ring, and wherein the heart valve is a mechanical heart valve comprising a valve member mounted for movement within the support to permit substantially unidirectional flow of blood through the mechanical heart valve.

* * * * *